United States Patent [19]

Engelbach et al.

[11] Patent Number: 4,814,479
[45] Date of Patent: Mar. 21, 1989

[54] PREPARATION OF AROMATIC NITRILES

[75] Inventors: Heinz Engelbach, Limburgerhof;
Roland Krokoszinski, Weisenheim;
Wolfgang Franzischka, Freinsheim;
Martin Decker, Ludwigshafen, all of
Fed. Rep. of Germany

[73] Assignee: BASF Aktiengesellschaft,
Ludwigshafen, Fed. Rep. of
Germany

[21] Appl. No.: 929,829

[22] Filed: Nov. 13, 1986

[30] Foreign Application Priority Data

Nov. 15, 1985 [DE] Fed. Rep. of Germany ....... 3540517

[51] Int. Cl.$^4$ .......................................... C07C 120/14
[52] U.S. Cl. .................................................. 558/328
[58] Field of Search ......................................... 538/328

[56]                References Cited
            U.S. PATENT DOCUMENTS 3,312,710  4/1967  Sakuyama et al. ............... 260/294.9
3,435,061  3/1969  Grasselli et al. .................... 260/465
3,637,797  1/1972  Decker et al. .................. 260/465 C
3,945,804  3/1976  Shang et al. ..................... 23/288 E

FOREIGN PATENT DOCUMENTS 222249  5/1987  European Pat. Off. ............ 558/328
1279012  9/1963  Fed. Rep. of Germany .
1643630  7/1967  Fed. Rep. of Germany .
1001674  8/1965  United Kingdom .
1065444  4/1967  United Kingdom .

Primary Examiner—Anton H. Sutto
Attorney, Agent, or Firm—Keil & Weinkauf

[57]                ABSTRACT

Aromatic nitriles, in particular phthalodinitriles, are prepared from an appropriately alkyl-substituted aromatic hydrocarbon by catalytic oxidation with oxygen or an oxygen-containing gas in the presence of ammonia at elevated temperatures in the vapor phase, in the presence of a catalyst which contains from 2 to 10% by weight of vanadium(V) oxide, from 1 to 10% by weight of antimony(III) oxide, from 0.02 to 2% by weight of an alkali metal oxide and alumina, by a process in which from 0.01 to 1.0% by weight of an alkaline earth metal, or of a compound of an alkaline earth metal, in particular barium or a barium compound, is added to the catalyst.

5 Claims, No Drawings

PREPARATION OF AROMATIC NITRILES

Preparation of aromatic nitriles

It is known that alkyl-substituted aromatic hydrocarbons can be reacted with oxygen and ammonia in the gas phase using catalysts. A large number of catalysts are known to be suitable for the reaction, these catalysts containing vanadium oxide as the active catalyst component, in addition to other metal oxides, e.g. oxides of tungsten, molybdenum, antimony, bismuth and titanium.

However, the selectivity and activity of the known catalysts are unsatisfactory. Moreover, they can only be used where the concentration of hydrocarbons in the reaction gas is not more than 2.0% by volume.

Another disadvantage of the known processes is that o-phthalodinitrile, which is important for the large scale industrial production of pigments, is virtually impossible to prepare by ammonoxidation of o-xylene by means of these processes, or can be obtained only in an unsatisfactory yield.

German patent 1,643,630 discloses a process which provides the aromatic mono- and dinitriles by ammonoxidation of the corresponding hydrocarbons.

The present invention is based on a process for the preparation of aromatic nitriles, in particular phthalodinitriles, from an appropriately alkyl-substituted aromatic hydrocarbon by catalytic oxidation with oxygen or an oxygen-containing gas in the presence of ammonia at elevated temperatures in the vapor phase, in the presence of a catalyst which contains from 2 to 10% by weight of vanadium(V) oxide, from 1 to 10% by weight of antimony (III) oxide, from 0.02 to 2% by weight of an alkali metal oxide and alumina.

The present invention relates to a process of this type in which the selectivity of the reaction and the activity of the catalyst are improved by adding from 0.01 to 1.0% by weight of an alkaline earth metal, in particular barium, to the catalyst.

Although German patent 1,279,012, U.S. Pat. No. 3,435,061 and British patent 1,065,444 disclose catalysts for the ammonoxidation of aromatic hydrocarbons to nitriles, the said catalysts also containing barium in addition to other active substances, the examples show that barium in conjunction with these combinations of substances results in a catalyst which has a substantially lower selectivity than the barium-free versions.

According to the invention, the alkaline earth metals, in particular barium, are added in an amount of from 0.01 to 1.0, preferably from 0.2 to 0.7, % by weight. Surprisingly, as a result of this addition, the selectivity is increased by about 5 mol % and the total oxidation to carbon dioxide and the combustion of ammonia are correspondingly reduced. Instead of Ba, it is also possible to use equivalent amounts of Sr, Ca or Mg.

Apart from the higher selectivity, another advantage of the novel process is that the volume concentration of the hydrocarbon in the reaction gas can be further increased and the partial pressure of the oxygen can be reduced without causing deposition of carbon compounds on the catalyst, which results in the rapid loss of catalyst activity. When the normal catalyst is used, the throughput of aromatic hydrocarbon per liter of reaction space can be increased by about 20% over the throughput possible to date, and at the same time the molar ratio of oxygen to hydrocarbon can be reduced. The improved process thus permits a higher production rate and lower costs in a given production plant.

The alumina used for the catalyst is obtained as follows: an aluminum hydroxide or aluminum oxide hydroxide, preferably an aluminum hydroxide obtained by precipitation with ammonia from a solution containing sulfuric acid, is dried in conventional manner, milled, pelletized and finally heated at from 600° to 1000° C., preferably from 800° to 900° C., for example for from 1/8 to 2 hours. The alumina prepared in this manner is a mixture of different modifications, in which the γ-modification predominates.

In addition to alumina, the catalysts contains from 2 to 10, advantageously from 3 to 7, % by weight of vanadium(V) oxide, from 1 to 10, advantageously from 3 to 7, % by weight of antimony(III) oxide and from 0.02 to 2% by weight of alkali metal oxides, advantageously from 0.1 to 1% by weight of an alkali metal oxide and from 0.01 to 1.0% by weight of an alkaline earth metal or of a compound of an alkaline earth metal, in particular barium or a barium compound. Suitable alkali metal oxides are oxides of lithium, sodium, potassium, rubidium and caesium and mixtures of these. Potassium oxide is preferably used. The percentages relate to the analytically determined contents of the particular substances and do not imply that these substances are present as such in the catalysts. On the contrary, it is possible, for example, that they have reacted with other oxides to form salt-like compounds.

To prepare the catalysts, the stated metal oxides can be applied to the alumina carrier by a conventional impregnation method, for example by impregnating the said carrier with a solution which contains the metal salts in the desired amount and then drying it. It is also possible to knead a finely milled alumina powder with the metal salt solution to give a paste, to dry the material beforehand and then break it up to the desired particle size. Antimony is preferably used as ammonium antimonyl tartrate or antimony nitrate and the alkaline earth metals in the form of their soluble salts, e.g. their nitrates, while vanadium may be present in the metal salt solution, for example, as the oxylate. The alkali metals are advantageously used in the form of hydroxides. The metal salts are then converted to the corresponding oxides, for example by heating the impregnated alumina is heated for a certain time, e.g. from 1 to 20 hours, for example at 200°–600° C., preferably 300°–450° C., in a stream of an oxygen-containing inert gas. The oxygen content of the gas mixture is expediently from 0.5 to 20, advantageously from 2 to 13, % by volume. Examples of suitable inert gases are nitrogen, carbon dioxide, steam and mixtures of these.

However, the catalysts are particularly advantageously obtained if the metal salts are applied to the carrier and decomposed in one operation, for example by adding the solution of the metal salts dropwise, at about 200°–450° C., preferably 250°–350° C., onto the carrier, which is kept fluidized by an oxygen-containing inert gas, for example a nitrogen/oxygen stream containing from 0.5 to 16, generally from 8 to 12, % by volume of oxygen.

Conventional oxidation conditions are suitable for the process.

Suitable starting materials are naphthalenes or benzenes which are monosubstituted or polysubstituted, advantageously monosubstituted, disubstituted or trisubstituted, by alkyl. Toluene or ethylbenzene gives benzonitrile, the xylenes give the phthalodinitriles, mesitylene gives the corresponding trimesotrinitriles, and alkyl naphthalenes give the corresponding naphthalenecarbonitriles; for example, 1-naphthonitrile is obtained from 1-methylnaphthalene and 1,8-naphthalenedicarbonitrile is obtained from 1,8-dimethylnaphthalene. It is also possible to use alkyl aromatics having longer alkyl side chains, for example up to 4 carbon atoms, although the process is less economical in this case.

The oxygen concentration in the reaction mixture may be varied within wide limits. Oxygen is preferably used in excess, for example in an amount which is 1.5 times the theoretically required amount. Ammonia is expediently used in excess, advantageously in an amount which is from 1.2 to 20 times the theoretically required amount.

The concentration of the alkyl-substituted aromatic hydrocarbon in the mixture of reactants is preferably from 1.8 to 5.0 % by volume, based on the total gaseous reaction mixture. Dilution with inert gases is also possible, this being achieved, for example, by using air as the oxygen-donating gas or by diluting the gas mixture with an inert gas, e.g. nitrogen.

The reaction is carried out at from 300° to 500° C., preferably from 420° to 4800° C. Particularly in the preparation of phthalodinitrile, it is advisable to maintain a temperature of from 430° to 480° C., since the content of imide and diamide decreases with increasing reaction temperature. Thus, when reaction temperatures of, for example, from 450° to 480° C. are used, it is possible to obtain dinitriles having a purity of more than 99.5%, so that subsequent purification and removal of imide and diamide can be dispensed with.

The residence time of the gas mixture over the catalyst can vary within wide limits, for example from 0.1 to 25 seconds, but is preferably about 0.5–5 seconds.

A fixed-bed catalyst or fluidized bed catalyst may be employed. The reaction is advantageously carried out under atmospheric pressure but may also be effected under slightly superatmospheric pressure, for example up to 1.5 atm gage pressure, or under slightly reduced pressure, e.g. 300 mmHg.

The reaction is carried out in a conventional manner, for example by passing the gas mixture over the catalyst at the reaction temperature, cooling the reaction gases and then depositing the nitriles by condensation, if appropriate by spraying in water. Because of the high purity, separate subsequent purification to remove imide and amide formed is not required in many cases.

EXAMPLE 1

750 ml of a catalyst having a particle size of from 0.05 to 0.3 mm are introduced into a quartz reactor which has a diameter of 60 mm and a length of 1000 mm and is provided with an external heater and a quartz frit for uniformly distributing the reaction gas. The catalyst is composed of 5.0% by weight of $V_2O_5$, 5.9% by weight of $Sb_2O_3$ 0.24% by weight of $K_2O$, 0.56% by weight of BaO and 88.3% by weight of $\gamma$-$Al_2O_3$. The reactor is heated to 470° C. and a gas mixture consisting of 3.25% by volume of o-xylene, 13% by volume of oxygen and 83.75% by volume of ammonia is passed through. The hot reaction gases are cooled to 70° C. with ammonia water in two wash towers arranged in series. An aqueous suspension of crystals is formed, from which the o-phthalodinitrile is isolated by filtration. 2,687 parts of o-xylene give 2,581 parts of o-phthalodinitrile and 195 parts of o-tolunitrile. By reacting the 195 parts of o-tolunitrile again with ammonia and oxygen, a further 170 parts of o-phthalodinitrile are obtained. The total yield of o-phthalodinitrile is 84.8 mol %, based on converted o-xylene.

COMPARATIVE EXAMPLE 750 ml of an alkaline earth metal-free comparative catalyst having a particle size of from 0.05 to 0.3 mm and composed of 5.0% by weight of $V_2O_5$, 6.8% by weight of $Sb_2O_3$ and 0.29% by weight of $K_2O$ on $\gamma$-alumina are introduced into the same apparatus. The catalyst is heated to 475° C. and a gas mixture consisting of 2.8% by volume of o-xylene, 11.7% by volume of oxygen and 85.5% by volume of ammonia is passed through. Deposition and working up are effected as in Example 1. 2,659 parts of o-xylene give 2,514 parts of o-phthalodinitrile and 240 parts of o-tolunitril. By reacting the 240 parts of o-tolunitrile again with oxygen and ammonia, a further 197 parts of o-phthalodinitrile are obtained. The total yield of o-phthalodinitrile is 78.3 mol %, based on o-xylene used.

EXAMPLE 2

Instead of the barium oxide, 0.5% by weight of magnesium oxide is added to catalyst described in Example 1, and the reaction of o-xylene with ammonia and oxygen is carried out under the same conditions as in Example 1.

3,378 g of o-xylene give 3,121 g of o-phthalodinitrile and 295 g of o-tolunitrile. By reacting the o-tolunitrile again, a further 262 g of o-phthalodinitrile are obtained. The total yield is 82.9 mol %.

EXAMPLE 3

Instead of the barium oxide, 0.15% by weight of calcium oxide is added to the catalyst described in Example 1, and the reaction of o-xylene with ammonia and oxygen is carried out under the conditions described there.

2,522 g of o-xylene give 2,372 g of o-phthalodinitrile and 206 g o-tolunitrile. By reacting the o-tolunitrile again, a further 180 g of o-phthalodinitrile are obtained. The total yield is 83.8 mol %.

We claim:

1. In a process for the production of an aromatic nitrile by the catalytic oxidation in the vapor phase of an alkyl-substituted aromatic hydrocarbon in the presence of ammonia and oxygen or an oxygen-containing gas at a temperature of from 300° to 500° C. and in the presence of a catalyst containing 2–10% by weight of vanadium (V) oxide, 1–10% by weight of antimony (III) oxide and 0.02 to 2% by weight of an alkali metal oxide, on an alumina carrier, the improvement which comprises:
   including in the catalyst composition from 0.01 to 1.0% by weight of an alkaline earth metal selected from the group consisting of Ba, Sr, Ca and Mg or a corresponding oxide of Ba, Sr, Ca or Mg.

2. The process of claim 1, wherein barium oxide is included in the catalyst composition.

3. The process of claim 2, wherein the alkyl-substituted aromatic hydrocarbon is benzene or naphthalene that is mono-, di- or trisubstituted by alkyl of 1 to 4 carbon atoms.

4. The process of claim 2, wherein the alkyl-substituted aromatic hydrocarbon is benzene or naphthalene that is mono-, di- or trisubstituted by methyl.

5. The process of claim 2, wherein the aromatic nitrile is o-phthalodinitrile and the alkyl-substituted aromatic hydrocarbon is o-xylene.

* * * * *